US00PP16976P2

(12) United States Plant Patent
Utecht

(10) Patent No.: US PP16,976 P2
(45) Date of Patent: Aug. 8, 2006

(54) ***PELARGONIUM* PLANT NAMED 'FISLORE'**

(50) Latin Name: *Pelargonium×hortorum*
Varietal Denomination: Fislore

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 29 days.

(21) Appl. No.: 11/167,835

(22) Filed: Jun. 27, 2005

(51) Int. Cl.
*A01H 5/00* (2006.01)

(52) U.S. Cl. ..... Plt./327

(58) Field of Classification Search ..... Plt./327
See application file for complete search history.

*Primary Examiner*—Kent Bell
(74) *Attorney, Agent, or Firm*—Jondle & Associates P.C.

(57) ABSTRACT

A new cultivar of *Pelargonium* particularly characterized by having brilliant-orange, semi-double, round flowers, relatively short peduncles, medium-green distinctly-zoned foliage, a relatively compact growth habit during greenhouse cultivation, a round to bushy plant habit, an early to mid-season flowering response, continuously flowering, and growing medium to tall in size is disclosed.

1 Drawing Sheet

Figure 1:
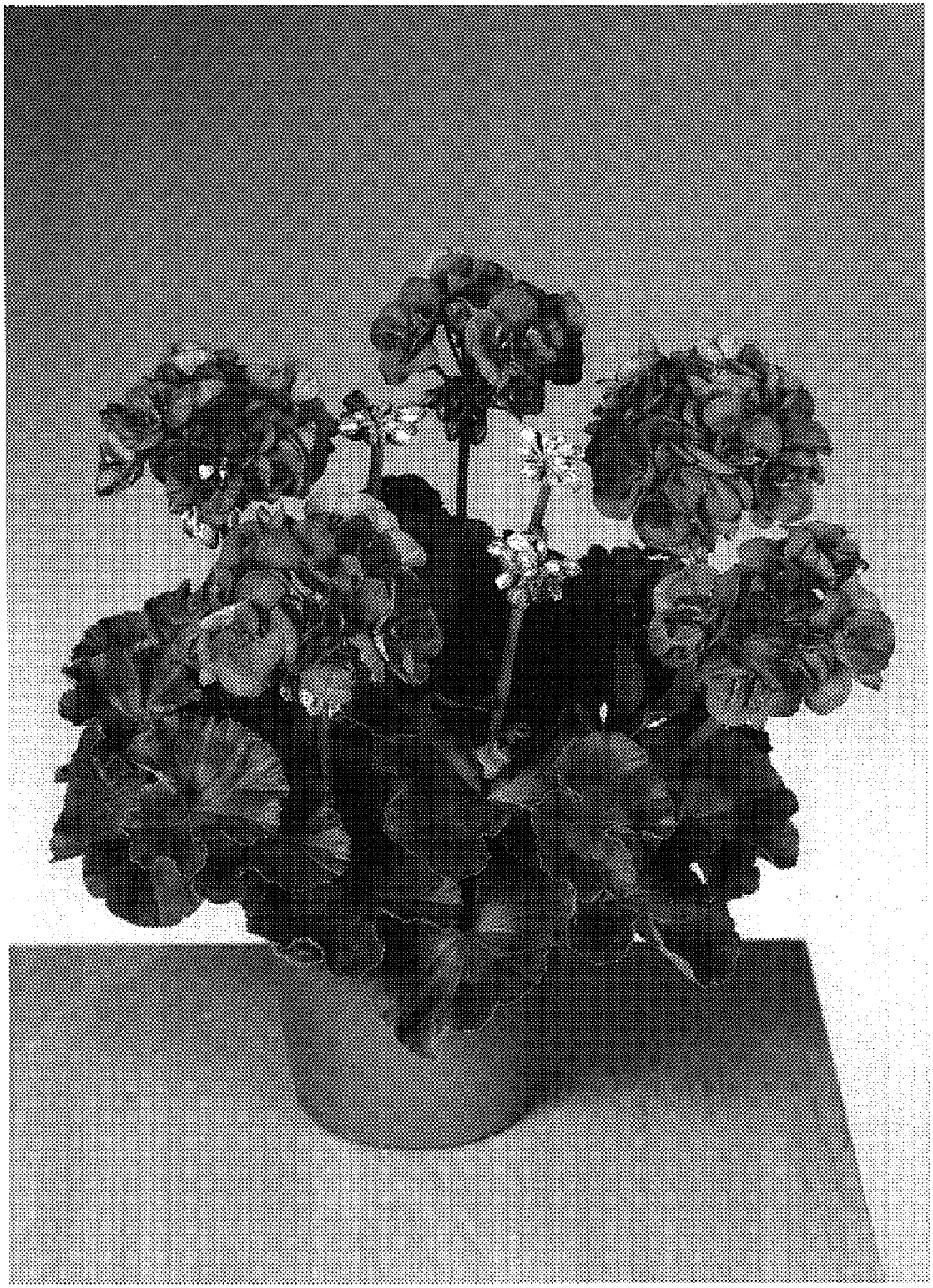

Genus and species: *Pelargonium×hortorum.*
Variety denomination: 'Fislore'.

BACKGROUND OF THE NEW PLANT

The present invention comprises a new and distinct cultivar of *Pelargonium,* botanically known as *Pelargonium× hortorum*, resp. a hybrid of *Pelargonium zonale* L'Héritier and hereinafter referred to by the cultivar name 'Fislore'. The new cultivar is a product of a planned breeding program which had the objective of creating new varieties having orange flowers, a good stability of flower color, medium green foliage, and suitable for the range of medium-sized varieties. 'Fislore' was discovered as a seedling resulting from a cross between the female parent, 'Fisrocky Orange' (U.S. Plant Pat. No. 12,365), which has orange-red, semi-double flowers, deep green foliage with narrow zonation, and a medium-sized plant habit and the male parent, 'Dueimap' (U.S. Plant Pat. No. 13,241), which has bright orange, semi-double flowers, grass-green foliage without or with very slight zonation, and a medium-sized plant habit.

The new cultivar was created in 2000 in Hillscheid, Germany, and has been asexually reproduced repeatedly by vegetative cuttings in Galdar, Gran Canaria, Spain, and Hillscheid, Germany, over a four-year period. 'Fislore' has not been observed under all possible environmental conditions, thus, the phenotype may vary significantly with variations in the environment such as temperature, light intensity, and day length. It has been found to retain its distinctive characteristics through successive asexual propagations. 'Fislore' reproduces true to type in successive generations of asexual reproduction.

Plant Breeder's Rights for this cultivar were applied for in Germany on Jun. 2, 2004. No sales or offers for sale of this cultivar were made before early July 2004.

SUMMARY OF THE INVENTION

The following are the most outstanding and distinguishing characteristics of this new cultivar when grown under normal commercial practices in Hillscheid, Germany.

1. Round, brilliant-orange, semi-double flowers with good stability of flower color;
2. Floriferous with medium-sized inflorescences on relatively short peduncles;
3. Medium-green foliage with distinct zonation;
4. Medium-sized or taller outdoors, with an initially compact habit;
5. A rounded and well-branched plant habit; and
6. An early to mid-season flowering response and fair rain resistance.

DESCRIPTION OF PHOTOGRAPH

This new *geranium* plant is illustrated by the accompanying photograph which shows blooms, buds, and foliage of the plant; the colors shown are as true as can be reasonably obtained by conventional photographic procedures. The photograph is of a twelve-week-old plant grown from rooted cuttings, in 14-cm pots, left un-pinched, and grown under greenhouse conditions which approximate those generally used in commercial practice.

FIG. 1. shows overall plant habit with blooms, buds, and foliage.

DESCRIPTION OF THE NEW CULTIVAR

The following detailed descriptions set forth the distinctive characteristics of 'Fislore'. The data which define these characteristics were collected from asexual reproductions carried out in Hillscheid, Germany. The plant history was taken on twelve-week-old, un-pinched plants in 14-cm pots in a greenhouse during mid-May. The color readings were determined under natural light in mid-May from flowers grown in a greenhouse. Color references are to The R.H.S. Colour Chart of The Royal Horticultural Society of London (R.H.S.) (2001).

DETAILED BOTANICAL DESCRIPTION

Classification:

*Botanical.—Pelargonium×hortorum,* resp. a hybrid of *Pelargonium zonale* L'Héritier.

*Common name.*—*Geranium.*

*Parentage.*—Female parent: 'Fisrocky Orange' (U.S. Plant Pat. No. 12,365). Male parent: 'Dueimap' (U.S. Plant Pat. No. 13,241).

Plant:

*Form.*—Shrub, self-branching, rounded shape.

*Branching habit.*—6–8 branches per plant.

*Height.*—13.5 cm for a 9 week-old plant (measured from base of stem to the tips of the branches, excluding the inflorescences).

*Width.*—24.5 cm for a 9 week-old plant.

*Time to produce a finished flowering plant.*—For spring flower response in Hillscheid, Germany, in 2004, plants have an average of 0.5 opened inflorescences 8 weeks after planting rooted cuttings.

*Outdoor plant performance.*—Plants continuously flower; a flower count in mid-May of 2004 in Hillscheid, Germany indicated about 4–5 inflorescences per plant.

Leaves:

*Arrangement.*—Alternate.

*Immature leaf.*—Color: medium green. Upper surface: RHS 137C (medium-green). Lower surface: RHS 137D (medium-green).

*Mature leaf.*—Color: Upper surface: RHS 137C (medium-green). Lower surface: RHS 137D. Length: 5.5 cm. Width: 8.7 cm.

*Zonation color.*—RHS 166A (brown) with a medium distinctness.

*Zonation diameter.*—Inner ring is 3.7 cm while the band or belt of zonation is 1.2 cm wide.

*Apex.*—Rounded.

*Base.*—Cordate.

*Shape.*—Kidney-shaped with weak lobes with narrow gap between lowest lobes and somewhat wavy.

*Margin.*—Bi-crenate.

*Texture.*—Upper surface is smooth, dull, and velvety.

Petioles:

*Length.*—5.5–6.0 cm.

*Diameter.*—0.3 cm.

*Color.*—RHS 143B (light-green).

*Texture.*—Covered with slight pubescence.

Stems:

*Length.*—7.0–9.0 cm.

*Internode length.*—0.5–1.0 cm.

*Color.*—RHS 143B (green).

*Texture.*—Appear smooth with slight pubescence.

Flower buds:

*Length.*—1.5 cm.

*Width.*—0.8 cm.

*Shape.*—Elliptical.

*Color of sepals* (*just before sepals unfold*).—RHS 143C (light-green).

*Color of petals* (*just before petals unfold*).—RHS 40A.

Inflorescence:

*Type.*—An umbel composed of 25–35 flowers.

*Umbel diameter.*—9.0 cm.

*Umbel depth* (*height*).—5.2 cm.

*Umbel shape.*—Semi-spherical.

*Lastingness of umbel on the plant.*—About 16 days.

*Peduncle.*—Length: 12.0 cm. Diameter: 4.0–5.0 mm. Texture: Weak pubescence. Color: RHS 143C (light-green).

*Pedicel.*—Length: 2.5 cm. Diameter: 1.5 mm. Texture: weak pubescence. Color: RHS 143C (light-green) near base and RHS 181A to RHS 181B (brown) at the upper end.

Corolla:

*Diameter.*—4.2 cm.

*Form.*—Semi-double.

*Shape.*—Round outline with both the upper petals and lower petals roughly of the same size and cup-shaped and having somewhat irregularly directed inner petals.

*Number of petals.*—8–9.

*Petaloids.*—Number: 0–2. Shape: Narrow. Color: RHS 40A to RHS 40B.

*Lastingness of individuals flowers on the plant.*—8 days at 18° C.

*Fragrance.*—None.

Petals:

*Upper petals.*—Length: 2.4–2.5 cm. Width: 2.0–2.1 cm. Color: Upper surface: Between RHS 40A and RHS 40B. Lower surface: From RHS 41A to RHS 41B (orange). Markings: RHS 46D (dull red) fine veins.

*Lower petals.*—Length: 2.2 cm. Width: 1.9–2.0 cm. Color: Upper surface: RHS 40B. Lower surface: Between RHS 41B and RHS 41C. Markings: Absent.

*Shape.*—Obovate.

*Apex.*—Rounded.

*Base.*—Acute.

*Margin.*—Entire or slightly crenated at the tip.

*Texture.*—Smooth, slightly glossy.

Sepals:

*Number.*—5.

*Length.*—0.9–1.0 cm.

*Width.*—0.3–0.4 cm for the largest upper sepal and 0.2–0.3 cm for the other sepals.

*Shape.*—Linear to lanceolate.

*Apex.*—Acute.

*Base.*—Truncate.

*Margin.*—Entire.

*Texture.*—Very weak pubescence.

*Color.*—For both upper and lower surfaces, RHS 143C (light-green) with a RHS 179A (brown) spot near base.

Reproductive organs:

*Androecium.*—Number of anthers: 2–5. Filament color: Mainly RHS 155D (white) to RHS 41B at upper end. Filament length: 7.0 mm. Pollen color: RHS 26A (yellow-orange). Pollen amount: Moderate.

*Gynoecium.*—Pistil number: 1. Pistil length: 7.0 mm. Stigma color: RHS 43D (salmon-pink). Stigma shape: 5–6 lobed. Style color: RHS 43D (salmon-pink). Style length: 3.0 mm. Style shape: Filiform, filament-like, with the lobes of the stigma at right angles.

Fruit/seed set: No seed set observed.

Disease and insect resistance: Average susceptibility or tolerance and no special observations made.

COMPARISON WITH KNOWN CULTIVARS

Of the many commercial cultivars known to the present inventor, the most similar in comparison to 'Fislore' are the varieties 'Fisrocky Orange' (U.S. Plant Pat. No. 12,365) and 'Fip 440' (U.S. Plant Pat. No. 13,964).

Cultivar 'Fislore' differs from the female parent 'Fisrocky Orange' (U.S. Plant Pat. No. 12,365) in that 'Fislore' has medium-green foliage and distinct zonation while 'Fisrocky Orange' has dark green foliage. Additionally, 'Fislore' has smaller flowers which are a deeper orange than the flowers of 'Fisrocky Orange'.

Cultivar 'Fislore' differs from the male parent 'Dueimap' (U.S. Plant Pat. No. 13,241) in that 'Fislore' lacks the small pink markings at the base of its upper petals that is characteristic of 'Dueimap'. The inflorescences of 'Fislore' are smaller in diameter by 1–1.5 cm and the peduncles are shorter by 5 cm. Additionally, the mature leaves of 'Fislore' develop distinct zonation, while the mature leaves of 'Dueimap' appear uniformly green.

Cultivar 'Fislore' differs from the commercial comparison variety 'Fip 440' (U.S. Plant Pat. No. 13,964) in that the plant habit of 'Fislore' is distinctly more compact and the peduncles are shorter. Additionally, the pedicels of 'Fislore' are partly brownish-red, while the pedicels of 'Fip 440' are uniformly green.

I claim:

1. A new and distinct cultivar of *Pelargonium* plant as shown and described herein.

* * * * *